(12) United States Patent
Zimmer

(10) Patent No.: US 8,298,211 B2
(45) Date of Patent: Oct. 30, 2012

(54) PUSH BUTTON PULL BACK DEVICE

(75) Inventor: Brian Zimmer, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 834 days.

(21) Appl. No.: 11/944,181

(22) Filed: Nov. 21, 2007

(65) Prior Publication Data

US 2009/0131914 A1 May 21, 2009

(51) Int. Cl.
*A61M 25/098* (2006.01)
(52) U.S. Cl. .......................... 604/529; 604/506; 606/200
(58) Field of Classification Search ................... 604/529, 604/506; 606/200
See application file for complete search history.

(56) References Cited

U.S. PATENT DOCUMENTS

| | | | | |
|---|---|---|---|---|
| 5,601,557 | A * | 2/1997 | Hayhurst | 606/232 |
| 2001/0034528 | A1* | 10/2001 | Foerster et al. | 606/116 |
| 2004/0122312 | A1* | 6/2004 | Chesbrough et al. | 600/431 |
| 2005/0085724 | A1* | 4/2005 | Sirimanne et al. | 600/431 |
| 2005/0251162 | A1* | 11/2005 | Rothe et al. | 606/153 |
| 2006/0241411 | A1* | 10/2006 | Field et al. | 600/431 |

FOREIGN PATENT DOCUMENTS

FR 2399853 * 4/1979

OTHER PUBLICATIONS

Non-Final Office Action mailed on May 10, 2011, U.S. Appl. No. 12/341,601, filed Dec. 22, 2008 (12 pages).
Final Office Action mailed on Oct. 14, 2011, for U.S. Appl. No. 12/341,601, filed Dec. 22, 2008 (22 pages).

* cited by examiner

*Primary Examiner* — Max Hindenburg
*Assistant Examiner* — Renee Danega
(74) *Attorney, Agent, or Firm* — Vista IP Law Group LLP

(57) ABSTRACT

A site marker deployment device includes a housing defining a first portion, an outer cannula at least partially interposed within the first portion and having a proximal end and a distal end defined by an outer cannula aperture, an inner member at least partially interposed within the outer cannula, a first biasing portion, a second biasing portion, wherein the second biasing portion will selectively urge the outer cannula to move proximally relative to the inner member, and a site marker selectively disposed within the outer cannula adjacent the inner member, near the distal end of the outer cannula. The first biasing portion will selectively urge a site marker at least partially within the outer cannula.

21 Claims, 6 Drawing Sheets

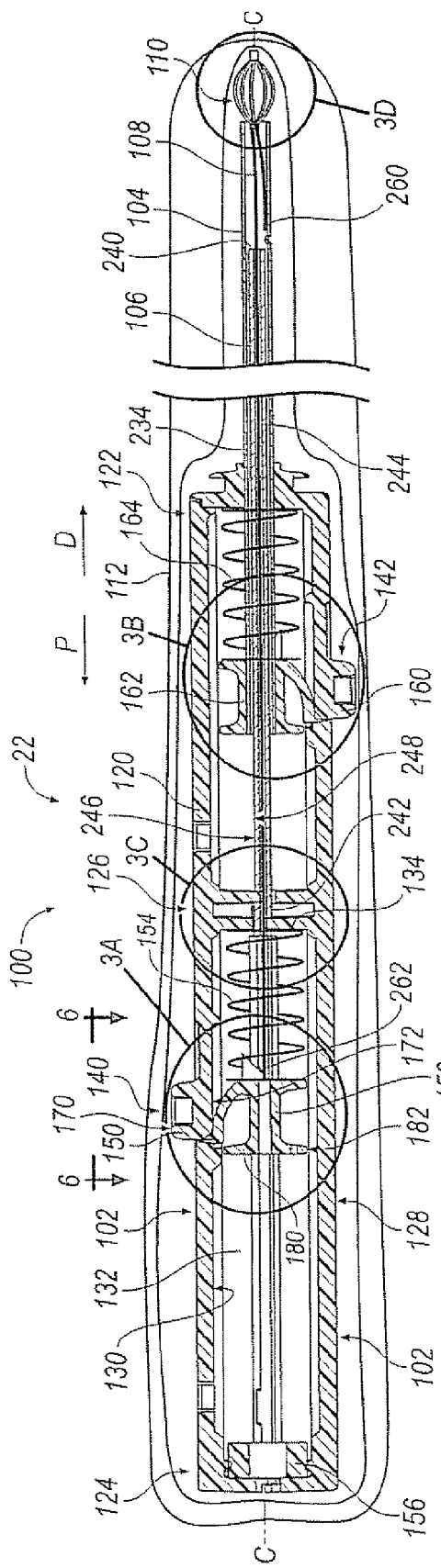
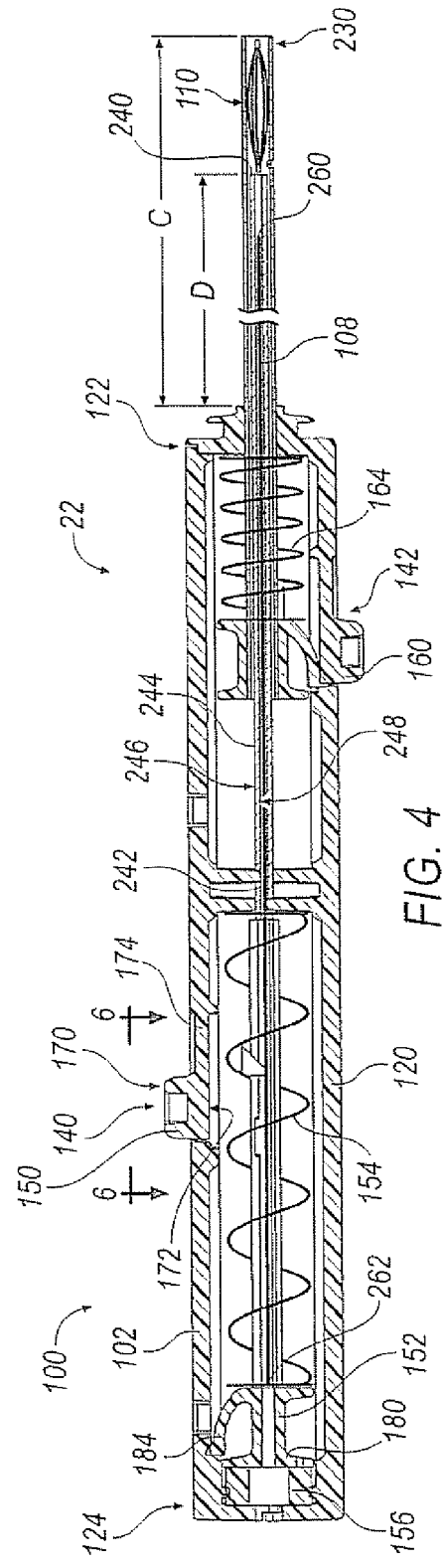
FIG. 3
FIG. 4

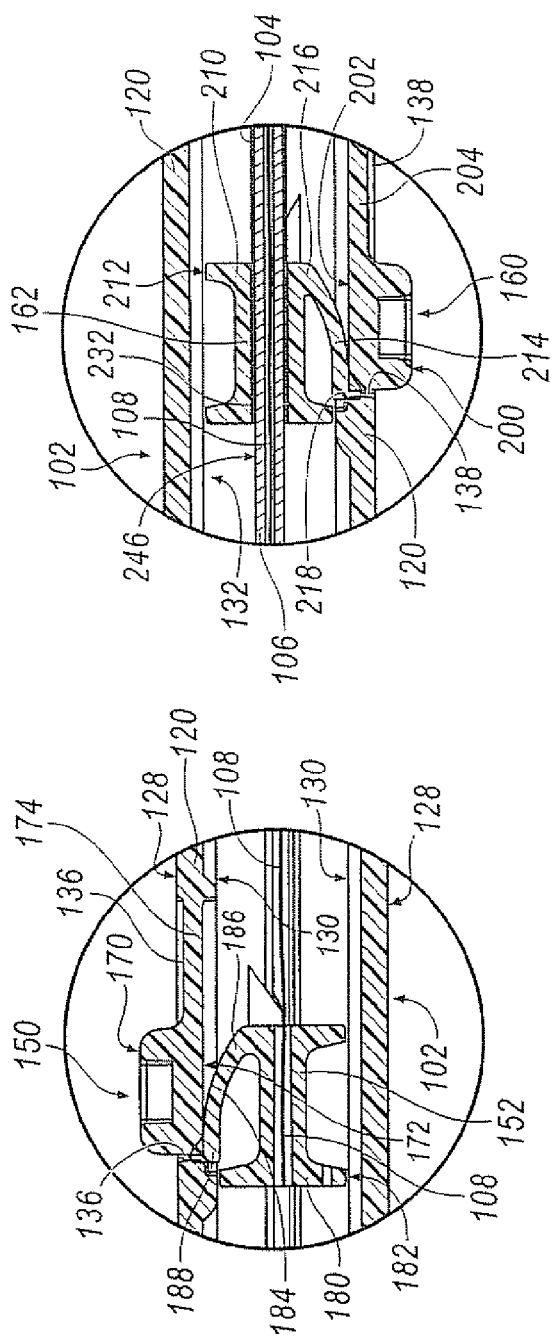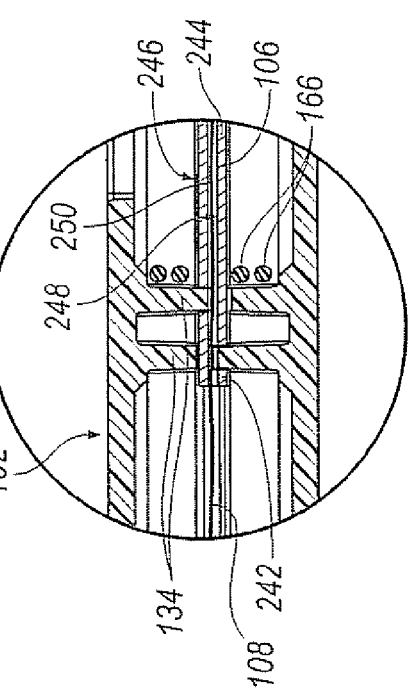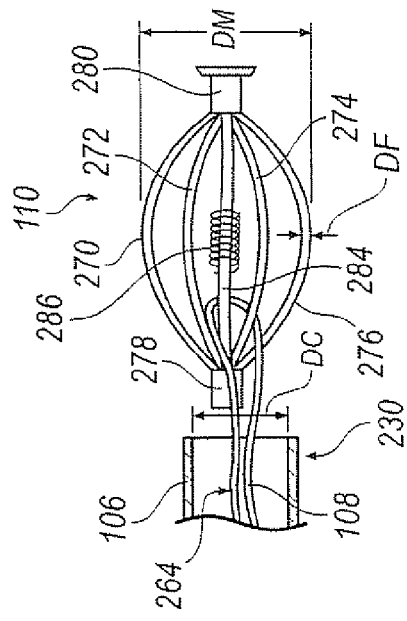

PUSH BUTTON PULL BACK DEVICE

TECHNICAL FIELD

The present disclosure relates generally to site markers for breast biopsy procedures. More specifically, the present disclosure relates to methods of deploying site markers.

BACKGROUND

In the diagnosis and treatment of breast cancer, it is often necessary to perform a biopsy to remove tissue samples from a suspicious mass. The suspicious mass is typically discovered during a preliminary examination involving visual examination, palpation. X-ray, magnetic resonance imaging (MRI), ultrasound imaging or other detection means.

When a suspicious mass is detected, a sample may be taken by biopsy, and then tested to determine whether the mass is malignant or benign. This biopsy procedure can be performed by an open surgical technique, or through the use of a specialized biopsy instrument such as stereotactic needle biopsy. To minimize surgical intrusion, a small specialized instrument such as a biopsy needle may be inserted in the breast while the position of the needle is monitored using fluoroscopy, ultrasonic imaging, X-rays, MRI or other suitable imaging techniques.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, and the original features of the tissue may have been removed or altered by the biopsy, it may be desirable to insert a site marker into the surgical cavity to serve as a landmark for future identification of the location of the lesion.

Commonly assigned U.S. application Ser. No. 11/242,334 discloses markers that use expandable filament portions to 'hold' a site marker in place within a biopsy cavity. That is, a site marker may include a bio-absorbable expandable portion, such as a suture, with a marker attached thereto, where the marker is visible under multiple modalities and the suture will inhibit migration of the marker within the biopsy cavity. The expandable portions of these structures typically define a site marker diameter that is greater than the outer diameter of a deployment cannula of a site marker deployment device. To insert a site marker within a biopsy site, the site marker is compressed (at least partially elastically deformed) to a dimension that will permit the site marker to be at least partially interposed within the cannula, the site marker and cannula are sterilized, the cannula is inserted within the biopsy canal such that the opening of the cannula is within the biopsy site, and the marker is deployed into the biopsy site. Once deployed, the site marker will expand as the marker exits the cannula in reaction to the elastic deformation. The site marker will expand until the elastic deformation is eliminated or portions of the site marker interfere with the inside portions of the biopsy cavity.

Precise placement of site markers is important for subsequent evaluation of the biopsy area. Current methods of marker deployment generally include locating the outer cannula of the biopsy instrument in the area of the lesion, then depressing a plunder or pushrod within the cannula to force the marker into a biopsy cavity. When the plunger or pushrod is depressed, however, the site marker may not be placed exactly where intended. For instance, if the cannula is placed at the center of a biopsy cavity, the marker may move from the center of the cavity to one side, making the marker more difficult to subsequently locate. Furthermore, varying amounts of pressure on the pushrod may cause the site marker to extend further into the cavity than desired.

Accordingly, there is a need for a site marker deployment device and/or method which allows more precise placement of a site marker within a biopsy cavity.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following, detailed description.

FIG. 3 is a partially sectioned side view of a site marker deployment device.

FIG. 3A is an enlarged view of portion 3A of FIG. 3.

FIG. 3B is an enlarged view of portion 3B of FIG. 3.

FIG. 3C is an enlarged view of portion 3C of FIG. 3.

FIG. 3D is an enlarged view of portion 3D of FIG. 3.

FIG. 4 is a partially sectioned side view of the site marker deployment device of FIG. 3 in a second configuration.

DETAILED DESCRIPTION

Figure 1:
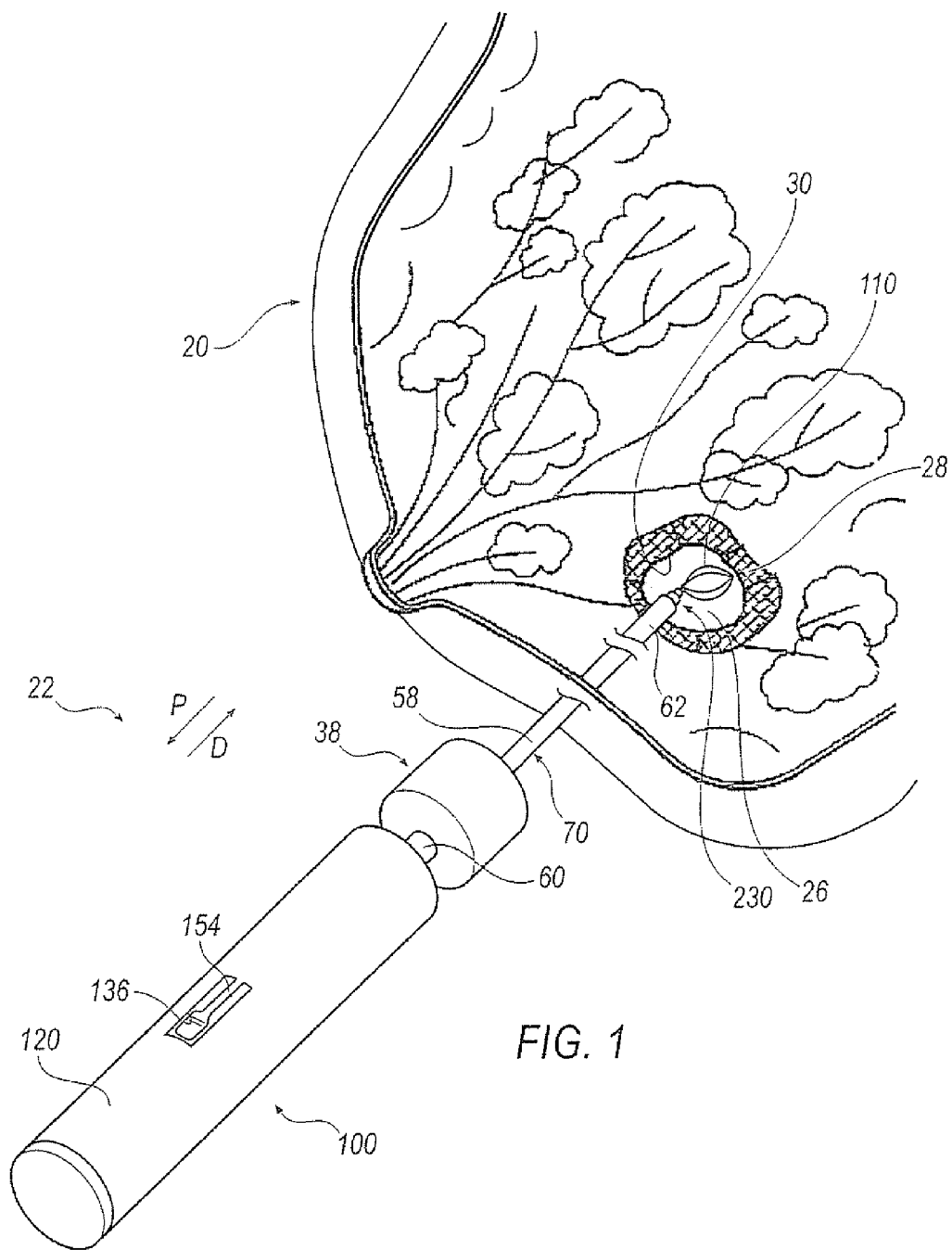
FIG. 1 is a perspective view of a biopsy site in a human breast showing the breast tissue section and one or more site markers being implanted in the biopsy cavity using a site marker delivery system.

Referring now to the drawings, illustrative embodiments are shown in detail. Although the drawings represent some embodiments, the drawings are not necessarily to scale and certain features may be exaggerated, removed, or partially sectioned to better illustrate and explain the present disclosure. Further, the embodiments set forth herein are not intended to be exhaustive or otherwise limit or restrict the claims to the precise forms and configurations shown in the drawings and disclosed in the following detailed description.

FIG. 1 illustrates a perspective view of a human breast, or tissue, 20 and a biopsy/site marker deployment system 22. As illustrated, the tissue 20 is being implanted with a site marker 110 at a desired location, or biopsy site, 26. In the embodiment illustrated, the biopsy site 26 is a lesion 28 from which a tissue sample (not shown) has been removed, resulting in a biopsy cavity 30.

Figure 2:
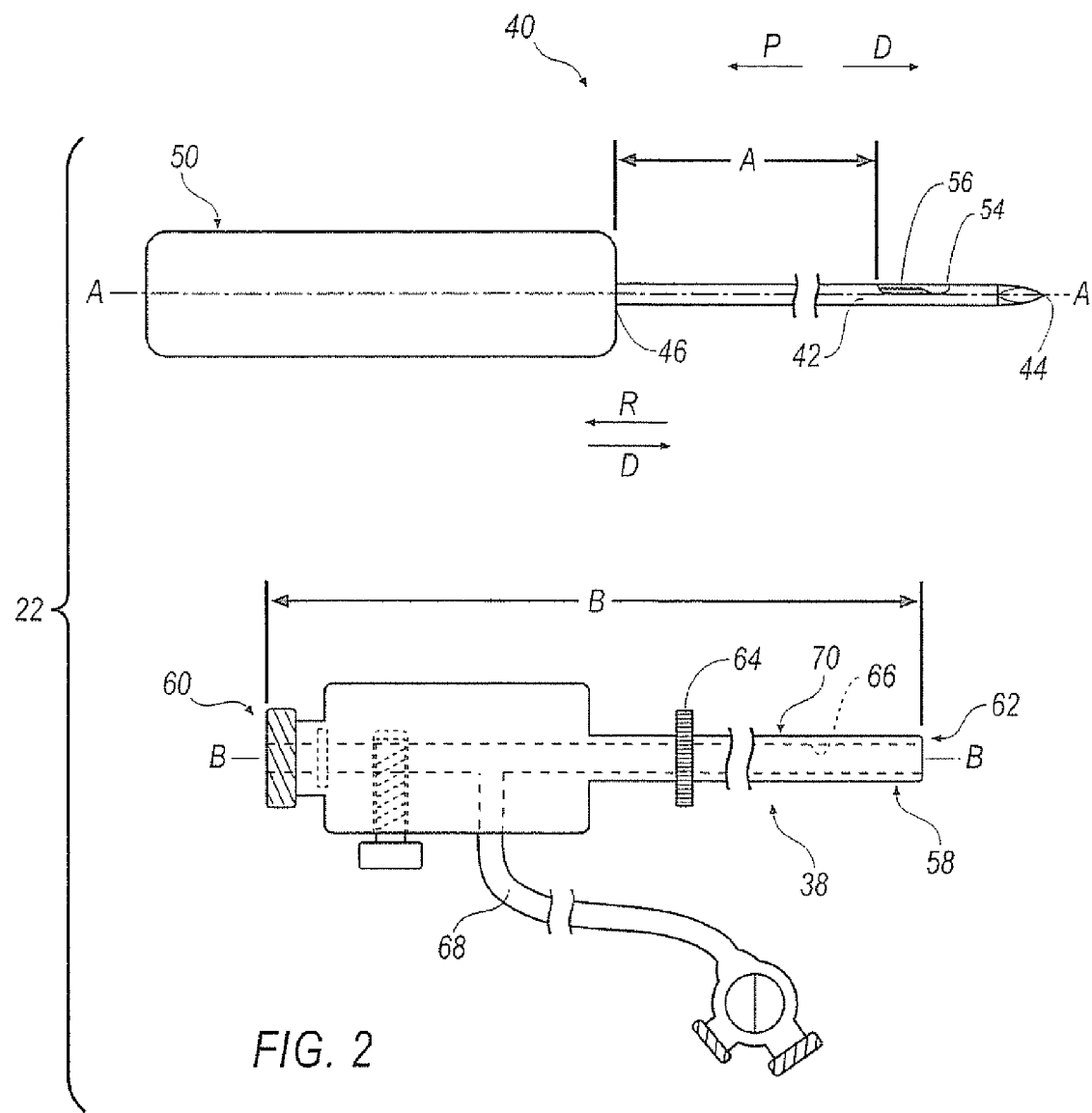
FIG. 2 is a top view of a biopsy device.

Referring to FIG. 2, the system 22 also includes an introducer assembly 38 and a biopsy device 40. The biopsy device 40 includes a biopsy cannula 42 having a length A extending from a distal biopsy cannula end 44 to a proximal biopsy cannula end 46. The biopsy device 40 may include a handle 50. The distal biopsy cannula end 44 includes an opening 54 for accessing tissue and a cutting portion 56 for severing a tissue sample, as is known. Exemplary biopsy devices may be found in U.S. Pat. Nos. 3,606,878; 4,708,147; and 6,758,824, the disclosures of which are incorporated by reference in their entireties.

The introducer assembly 38 includes an introducer cannula portion 58 generally defined by an axis B-B. The introducer assembly 38 extends from an open proximal end 60 to an open distal end 62, which is separated from proximal end 60 by a distance B. The introducer assembly 38 may be made from a medical grade resin or other MRI compatible material. A depth limiting member 64, such as a rubber o-ring, may be moveably disposed on introducer assembly 38 to limit the insertion depth of introducer assembly 38 into the patient's body. The introducer cannula portion 58 includes an inner lumen 66 therethrough, which may be in open communication with a fluid conduit 68 for supplying fluids, such as saline and anesthetics, or removing fluids, such as blood, from the patient's body. The introducer cannula portion 58 also includes an outer surface 70 that is inserted within tissue, such as tissue 20, as illustrated in FIG. 1. In the embodiments illustrated, the distance A is slightly greater than the distance B to permit the opening 54 to extend past the open distal end 62 of the introducer assembly 38.

FIGS. 1 and 3-5 illustrate a site marker deployment device 100. The device 100 includes a handle 102, a first member, or outer deployment cannula, 104, a second member, or inner member, 106 interposed at least partially within the deployment cannula 104, a retracting member 108, and at least one site marker 110. As illustrated in FIG. 3 the device 100 may be contained within a sterilized package 112.

One or more site markers 110 are implanted in the biopsy cavity 30 using the system 22. In one embodiment, the system 22 includes the biopsy device 40 (FIG. 2) and the site marker deployment device 100 (FIGS. 1, and 3-5) where each have a portion that is slidably advanced through the introducer assembly 38 (FIGS. 1 and 2). The introducer assembly 38 may remain in the tissue 20 after the biopsy device 40 is removed, which allows the deployment device 100 to be inserted within the tissue 20 and directed to the biopsy cavity 30 after the biopsy device 40 has been removed from the introducer assembly 38. Delivering the site marker 110 in the biopsy cavity 30 without withdrawing the introducer assembly 38 may reduce the amount of damage to tissue and enable more accurate placement of the site marker 110. The system 22 illustrated in FIGS. 1-7 is exemplary only and it is understood that the site marker embodiments disclosed herein are suitable for use with other marker delivery systems.

Referring to FIG. 3 the handle 102 includes an axis C-C, a body portion 120 extending along the axis C-C, a distal end portion 122, a proximal end portion 124, a central portion 126, an outer surface 128, an inside surface 130 at least partially defining a first portion, or hollow bore, 132, a central web portion 134, a retracting aperture 116 and a deployment aperture 138. Both the retracting aperture 136 (FIG. 3A) and the deployment aperture 138 (FIG. 3B) extend between the outer surface 128 and the inside surface 130. The device 100 also includes a retracting actuation portion 140 and a deployment actuation portion 142.

The retracting actuation portion 140, as best seen in FIGS. 3 and 3A, includes a retracting actuation member 150, a retracting hub portion 152, a retracting biasing portion 154, and a retracting bumper 156. The deployment actuation portion 142, as best seen in FIGS. 3 and 3B, includes a deployment actuation member 160, a deployment hub portion 162, a deployment biasing portion 164, and a deployment bumper 1566.

The retracting actuation member 150, as best seen in FIG. 3A, includes a first retracting surface 170 a second retracting surface 172, and a retracting tab portion 174. The retracting tab portion 174 extends between the body 120 and the retracting actuation member 150. In the embodiment illustrated, the retracting actuation member 150 is connected to the body 120 only by the retracting tab portion 174, and is radially displaceable toward the axis C-C as the retracting tab portion 174 deflects when a force is applied to the first retracting surface 170.

The retracting hub portion 152 is positioned within the first portion 132 and is axially moveable relative thereto. The retracting hub portion 152 includes a body 180 defined at least partially by an outer surface 182 that guides along at least a portion of the inside surface 130 of the handle 102, and a retracting restraining arm 184 that extends from the body 180. The retracting restraining arm 184 extends between a first end 186 at the body 180 and a second end 188. The second end 188 engages with a portion of the retracting aperture 136 to axially restrain the retracting biasing portion 154 (prevent a release of stored energy by the retracting biasing portion 154), as discussed in greater detail below. The retracting restraining arm 184 extends from the body 180 such that the second end 188 may be resiliently biased toward the axis C-C.

The retracting hub portion 152 is coupled to the retracting, member 108 such that movement of the retracting hub portion 152 toward the proximal end portion 124 will result in movement of the retracting member 108 toward the proximal end portion 124.

In the embodiment illustrated, the retracting biasing portion 154 is compressed (storing energy) between the retracting hub portion 152 and the central portion 126. The retracting biasing portion 154 biases (urges) the retracting hub portion 152 toward the proximal end portion 124 generally in the direction of the arrow P.

The deployment actuation member 160, as best seen in FIG. 3B, includes a first deployment surface 200 a second deployment surface 202, and a deployment tab portion 204. The deployment tab portion 204 extends between the body 120 and the deployment actuation member 160. In the embodiment illustrated, the deployment actuation member 160 is connected to the body 120 only by the deployment tab portion 204, and is radially displaceable toward the axis C-C as the deployment tab portion 204 deflects when a force is applied to the first deployment surface 200.

The deployment hub portion 162 is positioned within the first portion 132 and is axially moveable relative thereto. The deployment hub portion 162 includes a body 210 defined at least partially by an outer surface 212 that guides along at least a portion of the inside surface 130 of the handle 102, and a deployment restraining arm 214 that extends from the body 210. The deployment restraining arm 214 extends between a first end 216 at the body 210 and a second end 218. The second end 218 engages with a portion of the deployment aperture 138 to axially restrain the deployment biasing portion 164 (prevent a release of stored energy by the deployment biasing portion 164), as discussed in greater detail below. The deployment restraining arm 214 extends from the body 210 such that the second end 218 may be resiliently biased toward the axis C-C.

In the embodiment illustrated, the deployment biasing portion 164 is compressed (storing energy) between the deployment hub portion 162 and the central portion 126. The deployment biasing portion 164 biases (urges) the deployment hub portion 162 toward the proximal end portion 124 generally in the direction of the arrow P.

The deployment hub portion 162 is coupled to the deployment cannula 104 such that movement of the deployment hub portion 162 toward the proximal end portion 124 will result in movement of the deployment cannula 104 toward the proximal end portion 124.

In the embodiment illustrated, the retracting biasing portion 154 and the deployment biasing portion 164 are cylindrical helical coil springs with a generally circular cross section, although other biasing members may be used, including a single biasing member to perform the function of both the retracting biasing portion 154 and the deployment biasing portion 164.

The deployment cannula 104 includes a distal deployment cannula deployment cannula end 230, a proximal deployment cannula end 232 coupled to the deployment hub portion 162, a generally cylindrical body 234 (FIG. 7) extending therebetween and defined by an outer cannula surface 236, and an inner cannula surface 238. The inner member 106 includes a distal inner member end 240, an inner member proximal end 942 a generally cylindrical body 244 extending therebetween defined by a first inner member surface 246, and a second inner member surface 248. In the embodiment illustrated, the distal inner member proximal end 242 is coupled to the web portion 134 such that axial movement of the inner member 106 relative to the handle 102 is restrained. Also in the embodiment illustrated, the second inner member surface 248 defines a central bore 250 formed in the inner member 106 between the distal inner member end 240 and the distal inner member proximal end 242.

The retracting member 108 includes a retracting distal end 260, a retracting proximal end 262, and an outer surface 264 (FIG. 3D) extending between the retracting distal end 260 and the retracting proximal end 262. In the embodiment illustrated, the retracting member 108 is a length of wire with sufficient resiliency to pull the site marker 110 within the deployment cannula 104, as described in greater detail below. In one embodiment, the retracting proximal end 262 is coupled to the retracting hub portion 152 for movement therewith.

As best seen in FIG. 3D, in one embodiment the site marker 110 includes at least one generally elongated first filament member 270, and may include a first end connection 278 and a second end connection 280. In the embodiment illustrated, the site marker 110 also includes a second filament member 272, a third filament member 274, fourth filament member 276, and a fifth filament member 284 having a marker element, or permanent marker, 286 attached thereto. It is understood, however, that the fifth filament member 284 mid the permanent marker 286 may be omitted, and other selectively expandable site markers may be employed with the various embodiments of the deployment device 100. Each of the filament members 270, 272, 274, 276 is defined by a filament diameter DF. Other exemplary embodiments of site markers may be found in commonly assigned U.S. application Ser. No. 11/561,919, the disclose of which is incorporated by reference in its entirety.

Each of the filament members 270, 272, 274, 276, 284 extends between the first end connection 278 and the second end connection 280. In the embodiment illustrated, the fifth filament member 284 is shorter than the filament members 270, 272, 274, 276. Thus configured, the filament member 284 will remain generally straight while the filament members 270, 272, 274, 276 are resiliently curved.

In the embodiment depicted herein, at least one of the filament members 270, 272, 274, 276 are selectively configurable between a first deployed configuration (FIG. 5) and a first retracted configuration (FIG. 4). That is, the site marker 110 is configurable between the first deployed configuration (FIG. 5) and the first retracted configuration (FIG. 4) as at least one of the filament members 270, 272, 274, 276 are deformed, while not all filament members 270, 272, 274, 276 need be deformed to deform the site marker between the first deployed configuration and the first retracted configuration. In the first deployed configuration the site marker 110 can not be interposed within the deployment cannula 104. In the first retracted configuration the site marker may be interposed within the deployment cannula 104.

As illustrated in a sterilization configuration of FIG. 3, the site marker 110 may expand to a shape that is dictated by the configuration of the filament members 270, 272, 274, 276, 284. In the first deployed configuration of FIG. 5, the site marker 110 is defined by a shape where the filament members 270, 272, 274, 276 will interfere with tissue 20 of the biopsy cavity 30. That is, as the site marker 110 is deployed from the device 100, the filament members 270, 272, 274, 276 will deform away from the first retracted configuration of FIG. 4 and toward the sterilization configuration of FIG. 3. However, as the site marker 110 interferes with tissue surrounding the biopsy cavity 30, the site marker may not fully deform to the sterilization configuration of FIG. 3, but may deform to a deployed configurations such as the first deployed configuration of FIG. 5, depending on factors such as the geometry of the biopsy cavity 30 and the resiliency of the tissue 20. The interference of the tissue 20 and the filament members 270, 272, 274, 276 may retain the site marker 110 generally within the biopsy cavity 30 after the deployment device 100 is removed from the tissue 20.

In the sterilization configuration of FIG. 3, at least a portion of the filament members 270, 272, 274, 276 define a site marker dimension DM (measured generally normal to the axis C-C as in FIG. 3D) that is greater than the deployment cannula inside diameter DC (FIG. 3D). In one embodiment, the site marker dimension is about 1.5 times greater than the outside diameter of the deployment cannula 106. Further, the filament diameter DF is less than the deployment cannula inside diameter DC. In the first retracted configuration of FIG. 4, the site marker 110 may be full) interposed within the deployment cannula 104. As will be appreciated, the site marker 110 may be deformed into a plurality of retracted configurations depending upon how the filament members 270, 272, 274, 276 deform during insertion of the site marker 110 into the deployment cannula 104. Also as will be appreciated, the site marker 110 may be deformed into a plurality of deployed configurations depending upon how the filament members 270, 272, 274, 276 deform during deployment of the site marker 110 into the biopsy cavity 30, and the geometry of the biopsy cavity 30.

Thus positioned generally in the sterilization configuration of FIG. 3D, the site marker 110 may be sterilized while the filament members 270, 272, 274, 276 are deformed less than the deformation associated with the entire site marker 110 being wholly interposed within the deployment cannula 104. The system 22 may be supplied in the sterilization configuration of FIG. 3 and the deployment device 100 may then be sterilized prior to deployment of the site marker 110, or the system may be sterilized in the sterilization configuration of FIG. 3 and supplied and/or stored in this configuration awaiting deployment.

Figure 6:
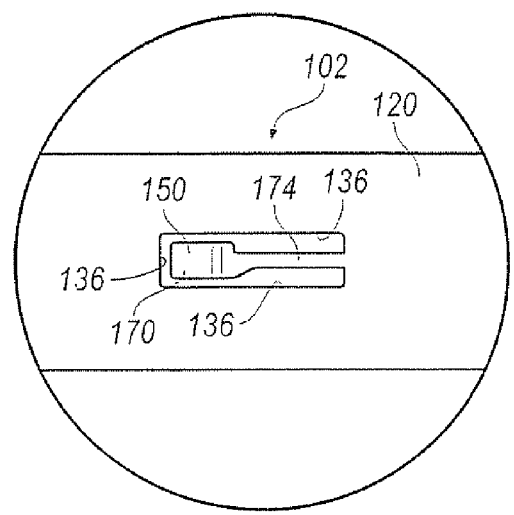
FIG. 6 is a view of the device of FIG. 3 taken generally along line 6-6 of FIG. 3.
Figure 7:
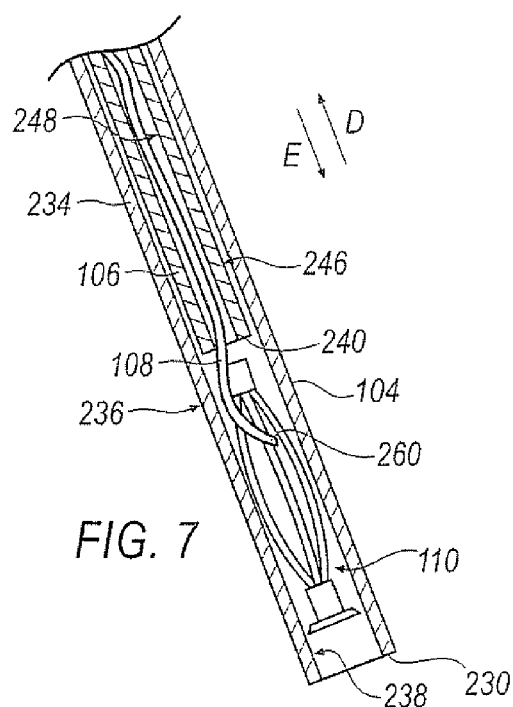
FIG. 7 is a partially sectioned view of a portion of the device of FIG. 3.
Figure 8:
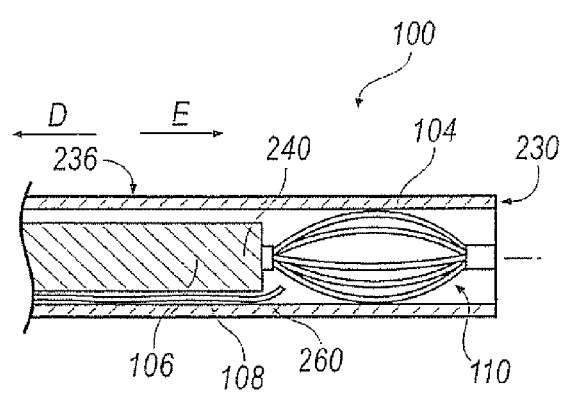
FIG. 8 is a partially sectioned view of a portion of a site marker deployment device.

FIG. 6 illustrates a top view of the retracting actuation member 150 where the retracting tab portion 174 extends between the retracting actuation member 150 and the body 120 of the handle 102. FIG. 7 illustrates an intermediate configuration between the sterilization configuration of FIG. 3 and the first retracted configuration of FIG. 4, where the retracting member 108 has pulled the site marker 110 at least partially within the deployment cannula 104 and the retracting member 108 is disengaging from the site marker 110 to permit the site marker to eject from the device 100. FIG. 8 is an alternative embodiment of the device 100 where the inner member 106 is illustrated without a central bore 250 formed therein, and the retracting member 108 is interposed between the first inner member surface 246 of the inner member 106 and inner cannula surface 238 of the deployment cannula 104.

One embodiment of a method of assembling the system 22 is as follows. The device 100 is assembled as described herein with the retracting member 108 extending from the distal deployment cannula end 230 of the deployment cannula 104. The retracting distal end 260 of the retracting member 108 is then threaded through the site marker 110 and the retracting distal end 260 is then interposed within the distal deployment cannula end 230, as generally shown in the exemplary embodiment of FIG. 3D. The device 100, as coupled to the site marker 110, is then sterilized, although the device 100 and the site marker 110 may be sterilized separately. The device 100 is then interposed within the sterilized package 112 and sealed, although the device 100 and the site marker 110 may be sterilized within the package 112 in the general configuration illustrated in FIG. 3.

One method of deploying a site marker, such as the site marker 110 is as follows. A user will open the package 112 and remove the device 100 (FIG. 3). The user will then depress the retracting actuation member 150 to retract the site marker 110 at least partially within the deployment cannula 104 (FIG. 4). When the retracting actuation member 150 is depressed (moved toward the axis C-C), the second retracting actuation surface 172 will interfere with the second end 188 of the retracting restraining arm 184 of the retracting hub portion 152, causing the second end 188 to move toward the axis C-C. As the retracting actuation member 150 is further depressed, the second end 188 will move sufficiently toward the axis C-C such that the second end 188 will disengage from the retracting aperture 136.

When the second end 188 disengages from the retracting aperture 136, the retracting biasing portion 154 urges the retracting hub portion 152 toward the proximal end portion 124 generally in the direction of the arrow P. The retracting hub portion 152, which is coupled to the retracting member 108, will urge the retracting member 108 generally in the direction of the arrow P. As the retracting member 108 is moved generally in the direction of the arrow P, the retracting member 108 will urge the site marker 110 within the distal deployment cannula end 230 of the deployment cannula 104. As the retracting member 108 is moved further generally in the direction of the arrow P (by the force exerted due to the release of energy by the retracting biasing portion 154), the retracting distal end 260 of the retracting member 108 twill disengage from the site marker 110 (FIG. 7) then move further toward the proximal end portion 124 of the handle 102 (such as seen, for example, in FIG. 4).

When the device 100 is generally in the configuration of FIG. 4, the user may then insert the deployment cannula 104 in the tissue 20. In the embodiment illustrated in FIG. 1, the deployment cannula 104 is at least partially inserted into the introducer assembly 38 such that the distal deployment cannula end 230 of the deployment cannula 104 extends at least slightly beyond the distal end 62 of the introducer assembly 38.

When the deployment device 100 is placed such that the site marker 110 is generally in the desired location within the tissue 20, as may be viewed under at least one of several modalities, the site marker may be deployed, or ejected from the deployment device 100.

To deploy the site marker 110, the user will depress the deployment actuation member 160. When the deployment actuation member 160 is depressed (moved toward the axis C-C), the second deployment surface 202 will interfere with the second end 218 of the deployment restraining arm 214 of the deployment hub portion 162, causing the second end 218 to move toward the axis C-C. As the deployment actuation member 160 is further depressed, the second end 218 will move sufficiently toward the axis C-C such that the second end 218 will disengage from the deployment aperture 138.

Figure 5:
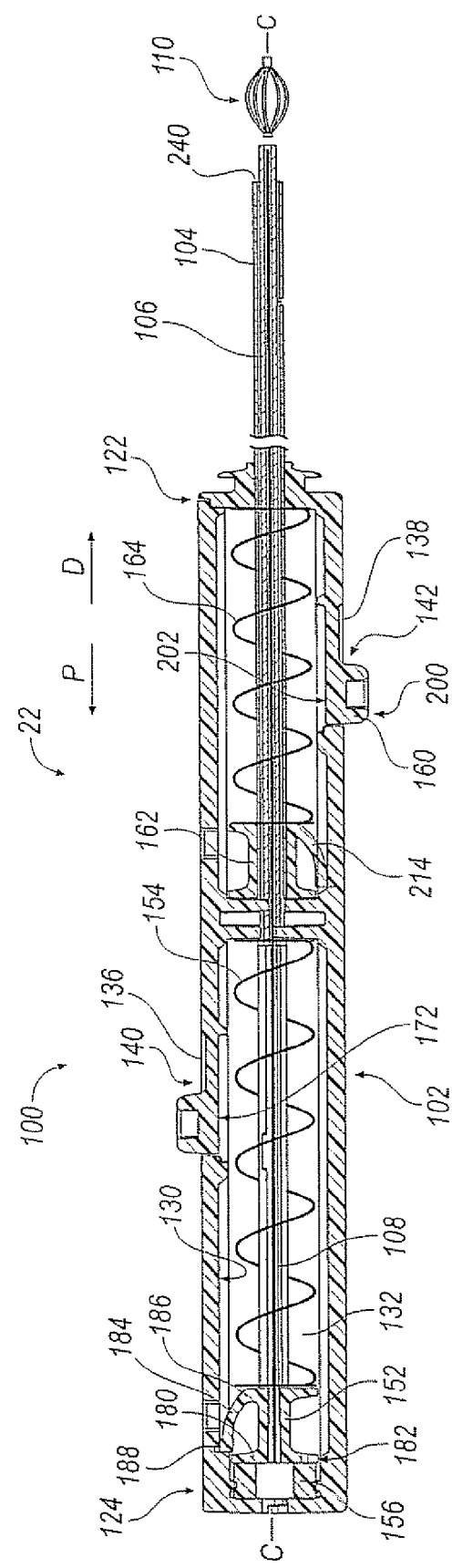
FIG. 5 is a partially sectioned side view of the site marker deployment device of FIG. 3 in a third configuration.

When the second end 218 disengages from the deployment aperture 138, the deployment biasing portion 164 urges the deployment hub portion 162 toward the proximal web portion 134 generally in the direction of the arrow P. The deployment hub portion 162, which is coupled to the deployment cannula 104, will urge the deployment cannula 104 generally in the direction of the arrow P. As the deployment cannula 104 is moved generally in the direction of the arrow P, the distal deployment cannula end 230 of the deployment cannula 104 move proximally (generally in the direction of the arrow P) at least partially past the site marker 110. As the deployment cannula 104 is moved further generally in the direction of the arrow P (by the force exerted due to the release of energy by the deployment biasing portion 164), the distal deployment cannula end 230 of the deployment cannula 104 will move past the distal inner member end 240 of the inter member 106 to disengage the site marker 110 from the deployment device 100 (FIG. 5).

Once released from the deployment device 100 and into the biopsy cavity 30, the site marker 110 automatically springs (due to the elastic deformation) into a deployed configuration (such as the first deployed configuration of FIG. 5) to a size and shape defined by the biopsy cavity 30. The resulting shape of the site marker 110 may enable the site marker 110 to be more readily visible under various imaging modalities. The deployment device 100 may be removed from the tissue. Further, the introducer assembly 38 may be removed simultaneously with the deployment device 100, as desired.

In general, the site markers described herein are made from biocompatible materials such as, but not limited to, titanium, stainless steel, and platinum. These materials have appropriate densities for radiographic imaging, appropriate surface characteristics for ultrasonic imaging, and appropriate magnetic characteristics for magnetic resonance imaging. The site markers are preferably made from titanium; however, it is understood that any suitable biocompatible material may be used. Alternatively, the site markers may be made of a bioabsorbable material with a permanent marker attached thereto. In the embodiments illustrated, the filament members have an aspect ratio of at least about 10:1, although other suitable aspect ratios may be used.

After installation in a biopsy cavity, over a predetermined time period such as three weeks to six months, the bio-absorbable materials described herein may be absorbed by the body, such that only permanent marker 286 remains within the body at the biopsy cavity 30. Because permanent markers are captured within the tissue 20 prior to absorption thereof by the body, permanent markers are restricted from migrating from within the tissue 20, such as within the biopsy cavity 30. Indeed, movement of a permanent marker is limited to the internal cavity immediately adjacent where a site marker is deployed. This insures that permanent markers remain within an area, such as the biopsy cavity 30 location, after the biopsy cavity 30 has closed to permit follow-up imaging of the biopsy site.

In other embodiments, a site marker may be constructed, at least in part, of a temperature dependent material. These site markers would not fully expand from the retracted configuration into the deployed configuration until heat is applied to the site marker. Deploying the site marker into a biopsy cavity provides a sufficient level of heat generated from the body to encourage the site marker to automatically expand into the second post-deployment configuration after deployment. Such materials include the shape-memory metal Nitonol™.

After installation in a biopsy cavity, such as biopsy cavity 30, over a predetermined time period such as three weeks to six months, the bio-absorbable filament members are absorbed by the body, such that only a permanent marker remains within the body within the biopsy cavity location, and is visible under one or more modalities such as X-ray, magnetic resonance imaging (MRI), or ultrasound imaging. Filament member may be absorbed by tissue ingrowth, leaving only a permanent marker, which may be retained in place by the tissue ingrowth.

In the embodiments illustrated, the permanent markers may be constructed of a material that is not absorbed by the body. Alternatively, the permanent markers may be a semi-permanent marker that bio-absorbs slower than the filament member. Because the movement of the permanent markers is restricted by the filament members prior to absorption thereof by the body, the permanent markers are restricted from migrating from within biopsy cavity. This insures that the permanent markers remain within the biopsy cavity to permit follow-up imaging of the biopsy site.

Since a site marker, such as the site marker 110, may be deployed with the aid of a MRI, the user will visually detect when the site marker has been deployed and may confirm that the site marker has been successfully deployed in the desired location Although the steps of the method of assembling the device 100 and deploying the site marker 110 are listed in an exemplary order, the steps may be performed ill differing orders or combined such that one operation may perform multiple steps. Furthermore, a step or steps may be initiated before another step or steps are completed, or a step or steps may be initiated and completed after initiation and before completion of (during the performance of) other steps.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A site marker deployment device, comprising:
 a housing defining a first portion;
 an outer cannula at least partially interposed within the first portion and having a proximal end and a distal end defining an outer cannula aperture;
 an inner member at least partially interposed within the outer cannula;
 a first actuator configured to at least partially release a first biasing portion to thereby selectively retract a site marker from outside of the outer cannula to at least partially within the outer cannula, such that the site marker is retained at least partially within the outer cannula;
 a second biasing portion configured to selectively urge the outer cannula to move proximally relative to the inner member and the site marker.

2. The device of claim 1, wherein the first biasing portion is selectively coupled to the site marker via a retracting portion, and wherein the retracting portion, when moved in a generally proximal direction, will urge the site marker at least partially within the outer cannula.

3. The device of claim 2, wherein the retracting portion, when moved further in the generally proximal direction, will disengage the site marker from the retracting portion.

4. The device of claim 1, wherein the inner member includes a hollow cannula and the retracting portion is at least partially interposed within the inner member.

5. The device of claim 1, wherein the target location is a lesion and the first biasing portion is a helical spring.

6. The device of claim 1, further comprising the site marker, wherein the site marker includes a plurality of resilient elongated portions joined at a first end connection and a second end connection.

7. The device of claim 6, wherein the site marker is configured to identify a biopsy location during at least one imaging procedure.

8. The device of claim 6, wherein the site marker includes a generally elongated first filament member, the first filament member selectively configurable between a retracted configuration, wherein the site marker is selectively interposed within the inner cannula, and a deployed configuration, where the site marker cannot be interposed within the inner cannula, and wherein a portion of the site marker is elastically deformed when the site marker is interposed within the inner cannula.

9. The device of claim 1, wherein the inner member is affixed to the housing such that the inner member does not move relative to the housing.

10. The device of claim 1, further comprising a retracting portion at least partially selectively interposed within the outer cannula and selectively coupling the first biasing portion to the site marker such that the site marker will be urged at least partially within the outer cannula as energy is released by the first biasing member.

11. The device of claim 1, further comprising a second actuator configured to at least partially release the second biasing portion.

12. A method of assembling a deployment device, comprising:
 interposing a first member at least partially within an outer cannula;
 interposing a retracting portion at least partially within an outer cannula;
 coupling a retracting biasing portion to the retracting portion such that a first actuator configured to at least partially release the retracting biasing portion will cause movement of at least a portion of the retracting portion to selectively retract a site marker from outside of the outer cannula to at least partially inside of the outer cannula, such that the marker is retained at least partially within the outer cannula;

coupling a deployment biasing portion to the outer cannula for moving the outer cannula in a generally axial direction relative to the first member and the site marker; and sterilizing the deployment device with a site marker not fully interposed within the outer cannula.

13. The method of claim 12, further comprising the steps of sterilizing at least one of the deployment device and the site marker while at least a portion of the site marker is not interposed within the outer cannula.

14. A method of deploying a marker, comprising:

actuating a first actuator to at least partially release a first biasing portion of a site marker deployment device, wherein the first biasing portion is coupled to a retracting portion configured to retract a site marker within an outer cannula, to thereby selectively retract a site marker from outside of the outer cannula to at least partially inside of the outer cannula, such that the marker is retained at least partially within the outer cannula;

inserting at least a portion of the outer cannula within a desired site marker location; and actuating a second actuator to at least partially release a second biasing portion of the site marker deployment device to retract the outer cannula such that a distal end of the outer cannula is moved toward a proximal end of the site marker deployment device relative to the site marker.

15. The method of claim 14, wherein at least a portion of the retracting portion is selectively interposed within an inner member.

16. The method of claim 14, wherein at least partially releasing the first biasing portion includes expanding a spring.

17. The method of claim 14, further comprising sterilizing at least one of the deployment device and the site marker while at least a portion of the site marker is not interposed within the outer cannula.

18. The method of claim 14, further comprising resiliently biasing at least a portion of the site marker as the site marker is urged within the outer cannula.

19. The method of claim 14, wherein releasing the second biasing portion of the site marker deployment device urges the outer cannula to move relative to an inner member, wherein the inner member is interposed within the outer cannula.

20. The method of claim 14, wherein actuating the first actuator of the site marker deployment device includes urging a sterilized site marker within the outer cannula.

21. The method of claim 14, further comprising removing at least a portion of a biopsy device from an introducer, and wherein inserting at least a portion of the outer cannula within a desired site marker location includes inserting a distal end of the outer cannula within the introducer.

* * * * *